United States Patent
Boaz

(10) Patent No.: US 6,906,212 B1
(45) Date of Patent: Jun. 14, 2005

(54) PHOSPHINE-PHOSPHORAMIDITE COMPOUNDS

(75) Inventor: Neil Warren Boaz, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 10/876,387

(22) Filed: Jun. 25, 2004

(51) Int. Cl.$^7$ .......................... C07F 17/02; B01J 31/00; C07C 5/03
(52) U.S. Cl. .......................... 556/22; 556/28; 556/144; 556/148; 564/12; 564/15; 502/162; 585/276; 568/846
(58) Field of Search ........................... 556/22, 28, 144, 556/148; 564/12, 15; 568/846; 585/276; 502/162

(56) References Cited

U.S. PATENT DOCUMENTS

| 6,590,115 B2 | 7/2003 | Boaz et al. |
| 6,720,281 B2 | 4/2004 | Leitner et al. |

OTHER PUBLICATIONS

Jia et al, Tetrahedron:Asymmetry, 2004, 15, pp. 2273–2278.
de Vries et al, Agnew. Chem. Int. Ed. Engl., 1996, 35, No. 20, pp. 2374–2376.
Malda et al, Org. Lett., 2001, Vo. 3, No. 8, pp. 1169–1171.
Alexakis et al, J. Am. Chem. Soc., 2002, 124, pp. 5262–5263.
Pena et al, J. Am. Chem. Soc., 2002, vol. 124, No 49, pp. 14552–14553.
Ohmura et al, J. Am. Chem. Soc., 2002, vol. 124, No. 51, pp. 15164–15165.
Urbaneja et al, Tetrahedron Letters, 2002, 43, pp. 7887–7890.
Jia et al, Tetrahedron Letters, 2002, 43, pp. 5541–5544.
Zeng et al, Tetrahedron:Asymmetry, 2002, 13, pp. 115–117.
Choi et al, Tetrahedron:Asymmetry, 2002, 13, pp. 801–804.
Li et al, Tetrahedron:Asymmetry, 2003, 14, pp. 2687–2691.
Boiteau et al, Org. Letters, 2003, vol. 5, No. 5, pp. 681–684.
Lopez et al, J. Am. Chem. Soc., 2003, vol. 125, No. 12, pp. 3426–3427.
Zhou et al, J. Org. Chem., 2003, vol. 68, No. 4, pp. 1582–1584.
Schmidt et al, Synthesis, 1984, pp. 53–60.
Schmidt et al, Synthesis, 1992, pp. 487–490.
Franci0 et al, Angew, Chem. Int. Ed., 2000, 39, No. 8, pp. 1428–1430.

*Primary Examiner*—Porfirio Nazario-Gonzalez
(74) *Attorney, Agent, or Firm*—Michael J. Blake; Bernard J. Graves, Jr.

(57) ABSTRACT

Disclosed are novel phosphine-phosphoramidite compounds which may be employed in combination with a catalytically-active metal to effect a wide variety of reactions such as asymmetric hydrogenations, asymmetric reductions, asymmetric hydroborations, asymmetric olefin isomerizations, asymmetric hydrosilations, asymmetric allylations, asymmetric conjugate additions, and asymmetric organometallic additions. Also disclosed are a process for the preparation of the phosphine-phosphoramidite compounds, metal complex compounds comprising at least one of the phosphine-phosphoramidite compounds and a catalytically-active metal and hydrogenation processes utilizing the metal complex compounds.

15 Claims, No Drawings

PHOSPHINE-PHOSPHORAMIDITE COMPOUNDS

FIELD OF THE INVENTION

This invention pertains to certain novel phosphorus-containing ligands useful in the formation of catalysts useful in carrying out a wide variety of reactions. More specifically, this invention pertains to a class of novel phosphine-phosphoramidite compounds which may be employed in combination with a catalytically-active metal to effect a wide variety of reactions such as asymmetric hydrogenations, asymmetric reductions, asymmetric hydroborations, asymmetric olefin isomerizations, asymmetric hydrosilations, asymmetric allylations, asymmetric conjugate additions, and asymmetric organometallic additions.

BACKGROUND OF THE INVENTION

Asymmetric catalysis is the most efficient method for the generation of products with high enantiomeric purity, as the asymmetry of the catalyst is multiplied many times over in the generation of the chiral product. These chiral products have found numerous applications as building blocks for single enantiomer pharmaceuticals as well as in some agrochemicals. The asymmetric catalysts employed may be enzymatic or synthetic in nature. The latter types of catalyst have much greater promise than the former due to much greater latitude of applicable reaction types. Synthetic asymmetric catalysts are usually composed of a metal reaction center surrounded by one or more organic ligands. The ligands usually are generated in high enantiomeric purity, and are the agents inducing the asymmetry. These ligands are, in general, difficult to make and therefore expensive. A notable exception are the chiral phosphine-aminophosphine ligands based on a phosphine-amine backbone described by Boaz et al., U.S. Pat. No. 6,590,115. These phosphine-aminophosphine compounds are useful as metal complexes for asymmetric catalysis and are readily prepared and air-stable.

Monodentate phosphoramidite ligands useful for asymmetric catalysis have been reported by de Vries, et al., *Angew. Chem. Int. Ed. Engl.* 1996, 35, 2374–2376; Malda, et al., *Org. Lett.* 2001, 3, 1169–1171; Alexakis, et al., *J. Am. Chem. Soc.* 2002, 124, 5262–5263; Pena, et al., *J. Am. Chem. Soc.* 2002, 124, 14552–14553; Ohmura, et al., *J. Am. Chem. Soc.* 2002, 124, 15164–15165; Urbaneja, et al., *Tetrahedron Lett.* 2002, 43, 7887–7890; Jia, et al., *Tetrahedron Lett.* 2002, 43, 5541–5544; Zeng, et al., *Tetrahedron:Asymm.* 2002, 13, 115–117; Choi, et al., *Tetrahedron:Asymm.* 2002, 13, 801–804; Li, et al., *Tetrahedron:Asymm.* 2003, 14, 2687–2691; Boiteau, et al., *Org. Lett.* 2003, 5, 681–684; Lopez, et al., *J. Am. Chem. Soc.* 2003, 125, 3426–3427; and Zhour, et al., *J. Org. Chem.* 2003, 68, 1582–1584.). These monodentate ligands have a single ligating group and have demonstrated moderate to high enantioselecitivity for a variety of asymmetric catalytic reactions including asymmetric hydrogenations. The monodentate ligands are, in general, prepared by reacting a diol with phosphorus trichloride followed by reaction with an amine (de Vries, et al., *Angew. Chem. Int. Ed. Engl.* 1996, 35, 2374–2376). Alternatively, the preparation of these types of ligands by the reaction of phosphorus trichloride with a preformed lithium amide (prepared from the amine and n-butyllithium) has been reported by Choi, et al., *Tetrahedron:Asymm.* 2002, 13, 801–804. There have been no reports of phosphine-phosphoramidite compounds prepared on a phosphine-amine backbone.

BRIEF SUMMARY OF THE INVENTION

We have discovered a class of novel phosphine-phosphoramidite compounds which may be employed in combination with a catalytically-active metal to effect a wide variety of reactions such as asymmetric hydrogenations, asymmetric reductions, asymmetric hydroborations, asymmetric olefin isomerizations, asymmetric hydrosilations, asymmetric allylations, asymmetric conjugate additions, and asymmetric organometallic additions. The novel compounds of the present invention have the formula:

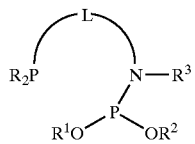

1 wherein
R and $R^3$ are substituted or unsubstituted, branched- or straight-chain $C_1$–$C_{20}$ alkyl, substituted or unsubstituted $C_3$–$C_8$ cycloalkyl, substituted or unsubstituted $C_6$–$C_{20}$ carbocyclic aryl, or substituted or unsubstituted $C_4$–$C_{20}$ heteroaryl having one to three heteroatoms wherein the heteroatoms are selected from sulfur, nitrogen, and oxygen;

$R^1$ and $R^2$ are, independently, achiral or substantially enantiomerically pure (i.e., an enantiomeric excess of 90% or greater) substituted or unsubstituted, branched- or straight-chain $C_1$–$C_{20}$ alkyl, substituted or unsubstituted $C_3$–$C_8$ cycloalkyl, substituted or unsubstituted $C_6$–$C_{20}$ carbocyclic aryl, substituted or unsubstituted $C_4$–$C_{20}$ heteroaryl having one to three heteroatoms wherein the heteroatoms are selected from sulfur, nitrogen, and oxygen, or $R^1$ and $R^2$ collectively represent a substituted or unsubstituted achiral, chiral and racemic, or substantially enantiomerically pure divalent alkylene, cycloalkylene or arylene radical wherein the chain of carbon atoms in the main chain that joins the amidite oxygen atoms in formula 1 contains 2 to about 8 carbon atoms;

L is a divalent chiral radical selected from substituted or unsubstituted, branched- or straight-chain $C_1$–$C_{20}$ alkylene, substituted or unsubstituted $C_3$–$C_8$ cycloalkylene, substituted or unsubstituted $C_6$–$C_{20}$ carbocyclic arylene, substituted or unsubstituted $C_4$–$C_{20}$ heteroarylene having one to three heteroatoms wherein the heteroatoms are selected from sulfur, nitrogen, and oxygen, or substituted or unsubstituted metallocenylmethylene, wherein L is substantially enantiomerically pure.

A second embodiment of our invention is a process for the preparation of phosphine-phosphoramidite compounds of formula 1 which comprises the steps of:
(1) contacting an amine having the formula

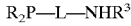 4 with phosphorus trihalide $PX_3$ in an inert organic solvent to obtain an intermediate dihalide having formula 5

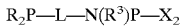 5 and (2) contacting intermediate dihalide 5 with one or more hydroxyl containing reactants having formulas 6, 7 or 8

$$R^1—OH, \qquad\qquad 6$$
$$R^2—OH \text{ or} \qquad\qquad 7$$
$$HO—R^1—R^2—OH \qquad\qquad 8$$

wherein

R, $R^1$, $R^2$ and $R^3$ are defined above; and

X is halogen, preferably bromo or, especially, chloro.

A third embodiment of the present invention pertains to metal complex compounds comprising a phosphine-phosphoramidite compound of formula 1 and a catalytically-active metal selected from Group VIII metals.

A fourth embodiment of the present invention pertains to a process for the hydrogenation of a hydrogenatable compound which comprises contacting the hydrogenatable compound with hydrogen in the presence of a catalyst complex of a phosphine-phosphoramidite compound of formula 1 and a catalytically-active metal.

DETAILED DESCRIPTION

The alkyl groups that may represent each of R, $R^1$, $R^2$ and $R^3$ may be straight- or branched-chain aliphatic hydrocarbon radicals containing from one up to about 20 carbon atoms and may be substituted, for example, with one to three groups selected from $C_1$–$C_6$-alkoxy, cyano, $C_2$–$C_6$-alkoxycarbonyl, $C_2$–$C_6$-alkanoyloxy, aryl and halogen. The terms "$C_1$–$C_6$-alkoxy". "$C_2$–$C_6$-alkoxycarbonyl", and "$C_2$–$C_6$-alkanoyloxy" are used to denote radicals corresponding to the structures —$OR^7$, —$CO_2$ $R^7$, and —$OCOR^7$, respectively, wherein $R^7$ is $C_1$–$C_6$-alkyl or substituted $C_1$–$C_6$-alkyl. The term "$C_3$–$C_8$-cycloalkyl" is used to denote a saturated, carbocyclic hydrocarbon radical having three to eight carbon atoms. The aryl groups that each of R, $R^1$, $R^2$ and $R^3$ may represent include phenyl, naphthyl, anthracenyl or phenyl, naphthyl, or anthracenyl substituted with one to three substituents selected from $C_1$–$C_6$-alkyl, substituted $C_1$–$C_6$-alkyl, $C_6$–$C_{10}$ aryl, substituted $C_6$–$C_{10}$ aryl, $C_1$–$C_6$-alkoxy, halogen, cyano, $C_1$–$C_6$-alkanoyloxy, $C_1$–$C_6$-alkylthio, $C_1$–$C_6$-alkylsulfonyl, trifluoromethyl, $C_2$–$C_6$-alkoxycarbonyl, $C_2$–$C_6$-alkanoylamino and —O—$R^8$, S—$R^8$, —$SO_2$—$R^8$, —$NHSO_2R^8$ and —$NHCO_2R^8$, wherein $R^8$ is phenyl, naphthyl, or phenyl or naphthyl substituted with one to three groups selected from $C_1$–$C_6$-alkyl, $C_6$–$C_{10}$ aryl, $C_1$–$C_6$-alkoxy and halogen.

The $C_4$–$C_{20}$ heteroaryl radicals described herein include a 5- or 6-membered aromatic ring containing one to three heteroatoms selected from oxygen, sulfur and nitrogen. Examples of such heteroaryl groups are thienyl, furyl, pyrrolyl, imidazolyl, pyrazolyl, thiazolyl, isothiazolyl, oxazolyl, isoxazolyl, triazolyl, thiadiazolyl, oxadiazolyl, tetrazolyl, pyridyl, pyrimidyl, benzoxazolyl, benzothiazolyl, benzimidazolyl, indolyl and the like. The heteroaryl radicals may be substituted, for example, with up to three groups such as $C_1$–$C_6$-alkyl, $C_1$–$C_6$-alkoxy, substituted $C_1$–$C_6$-alkyl, halogen, $C_1$–$C_6$-alkylthio, aryl, arylthio, aryloxy, $C_2$–$C_6$-alkoxycarbonyl and $C_2$–$C_6$-alkanoylamino. The heteroaryl radicals also may be substituted with a fused ring system, e.g., a benzo or naphtho residue, which may be unsubstituted or substituted, for example, with up to three of the groups set forth in the preceding sentence. The term "halogen" is used to include fluorine, chlorine, bromine, and iodine.

$R^1$ and $R^2$ collectively may represent a divalent alkylene, cycloalkylene or arylene radical wherein the chain of carbon atoms, e.g., an alkylene or alkenylene group, in the main chain that joins the amidite oxygen atoms in formula 1 contains 2 to about 8 carbon atoms. More specifically, a divalent radical collectively represented by $R^1$ and $R^2$ may contain a total of 2 to about 20 carbon atoms and may be substituted or unsubstituted and connects the two amidite oxgen atoms by a chain of 2 to about 8 carbons. The divalent radical collectively represented by $R^1$ and $R^2$ may be substituted with the substituents described in the preceding paragraph. Examples of such divalent radicals include 1,2-ethanediyl (ethylene), 1,3-propanediyl (trimethylene), 1,4-butanediyl (tetramethylene), 2,3-butanediyl, 2,2'-biphenyldiyl, 1,1'-binaphthyl-2,2'-diyl and the like wherein the divalent radical may be achiral, chiral and racemic, or chiral and substantially enantiomerically pure.

The skilled artisan will understand that each of the references herein to groups or moieties having a stated range of carbon atoms, such as "$C_1$–$C_6$-alkyl," includes not only the $C_1$ group (methyl) and $C_6$ group (hexyl) end points, but also each of the corresponding individual $C_2$, $C_3$, $C_4$ and $C_5$ groups. In addition, it will be understood that each of the individual points within a stated range of carbon atoms may be further combined to describe subranges that are inherently within the stated overall range. For example, the term "$C_1$–$C_6$-alkyl" includes not only the individual moieties $C_1$ through $C_6$, but also contemplates subranges such as "$C_2$–$C_5$-alkyl."

A preferred class of the novel compounds provided by the present invention have formulas 2 or 3 (the enantiomer of 2)

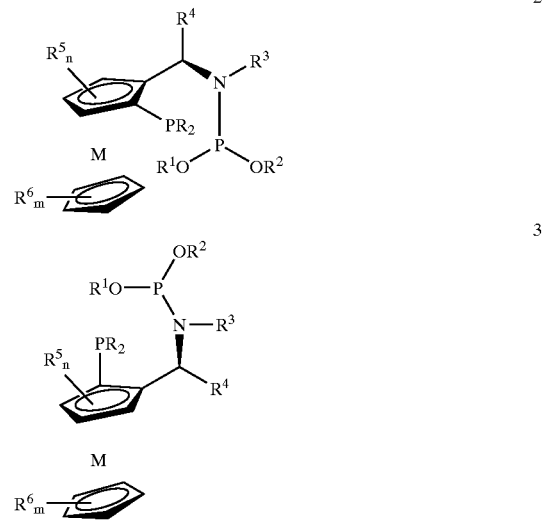

wherein

R, $R^1$, $R^2$ and $R^3$ are as defined above;

$R^4$, $R^5$, and $R^6$ are, independently, hydrogen, substituted or unsubstituted, branched- or straight-chain $C_1$–$C_{20}$ alkyl, substituted or unsubstituted $C_3$–$C_8$ cycloalkyl, substituted or unsubstituted $C_6$–$C_{20}$ carbocyclic aryl, or substituted or unsubstituted $C_4$–$C_{20}$ heteroaryl having one to three heteroatoms wherein the heteroatoms are selected from sulfur, nitrogen, and oxygen;

n is 0 to 3;

m is 0 to 5; and

M is a metal selected from Groups IVB, VB, VIIB, VIIB or VIII.

Examples of the unsubstituted or substituted groups represented by $R^4$, $R^5$, and $R^6$ are set forth above in the description of the radicals that R, $R^1$, $R^2$ and $R^3$ may represent. Examples of the metals represented by M include iron, ruthenium, and osmium.

A more preferred group of the novel phosphine-phosphoramidite compounds have formulas 2 or 3 (the enantiomer of 2)

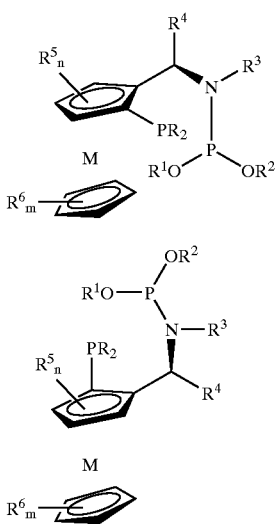

wherein
R is aryl, most preferably phenyl, $R^1$ is aryl, most preferably phenyl, 4-methoxyphenyl, or 4-trifluoromethylphenyl; $R^2$ is aryl, most preferably phenyl, 4-methoxyphenyl, or 4-trifluoromethylphenyl, or $R^1$ and $R^2$ are collectively 1,2-ethanediyl, 1,3-propanediyl, 1,2-benzenediyl, 2,2'-biphenyldiyl, racemic 1,1'-binaphthyl-2,2'-diyl, (R,R)-1,1'-binaphthyl-2, 2'-diyl, or (S,S)-1,1'-binaphthyl-2,2'-diyl; $R^3$ is hydrogen, $C_1$–$C_6$ alkyl, or aryl, most preferably methyl; $R^4$ is hydrogen or $C_1$–$C_6$ alkyl, most preferably methyl; $R^5$ and $R^6$ are hydrogen;

n is 0;

m is 0; and

M is iron.

A further embodiment of our invention is a process for preparing phosphine-phosphoramidite compounds having formula 1

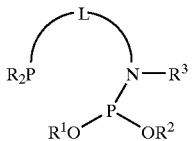

which comprises
(1) reacting an amine having formula 4

$$R_2P-L-NHR^3 \quad \quad 4$$

with phosphorus trihalide $PX_3$ in an inert organic solvent to obtain an intermediate dihalide compound of formula 5

$$R_2P-L-N(R^3)P-X_2 \quad \quad 5$$

and
(2) contacting dihalide 5 with one or more hydroxyl-containing reactants having formulas 6, 7 or 8

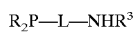

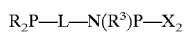

wherein
R, $R^1$, $R^2$ and $R^3$ are as defined above; and
X is a halogen, preferably bromo or, especially, chloro. As noted below, steps (1) and (2) may optionally be carried out in the presence of an acid acceptor.

The process may be carried out in an inert, organic solvent such as a cyclic or acyclic ether, e.g., diethyl ether, diisopropyl ether, tert-butyl methyl ether, or tetrahydrofuran; aromatic hydrocarbons, e.g., benzene, toluene, or xylene; aliphatic and alicyclic hydrocarbons, e.g., hexane, heptane, or cyclohexane; or mixtures of any 2 or more of the foregoing. The preferred solvent is toluene. Step (1) of the process may be carried out at a temperature between about −100° C. and the boiling point of the solvent, preferably about −80° to 40° C.

Step (1) may optionally be carried out in the presence of an acid acceptor, preferably a $C_3$–$C_{15}$ tertiary amine or a pyridine, with the preferred amine being triethylamine. The relative amounts of reactant 4 and phosphorus trihalide $PX_3$ employed in step (1) typically provides a reactant 4 to phosphorus trihalide $PX_3$ mole ratio of about 0.5:1 to 4:1, preferably about 1:1 to 1.5:1. The amount of acid acceptor is at least 1.0 moles per mole of reactant 4, and is typically 1.0 to 2.0 moles of acid acceptor per mole of reactant 4. Although not expressly determined, results obtained from subsequent reactions indicate that the intended dihaloaminophosphine 5 produced in this reaction (i.e., when L is a metallocenylmethylene) is substantially uncontaminated with monohalodiaminophosphine and triaminophosphine. This is surprising, as a statistical mixture of these species might be expected. Although not wishing to be bound by theory, these results may be due to the steric congestion engendered by the amine used which limits the number of amines that can react with the phosphorus trihalide. Although not necessary, dihalide intermediate 5 may be isolated before conducting the second step of the process.

Step (2) of the process may be carried out at a temperature between about −100° C. and the boiling point of the solvent, and preferably at about −80° to 40° C. This step may also be carried out in the optional presence of an acid acceptor, preferably a $C_3$–$C_{15}$ tertiary amine or a pyridine, with the preferred amine being triethylamine. The amount of acid acceptor is typically 2.0 to 5.0 moles of acid acceptor per mole of intermediate 5. The amount of hydroxyl reactant(s) employed normally should provide at least 2 equivalents of hydroxyl and up to 10 equivalents of hydroxyl per mole of dihalide intermediate 5. The preferred amount is 2 equivalents of hydroxyl reactant(s) per mole of dihalide 5. The hydroxyl reactants 6 and 7 preferably are the same, and preferably are phenol, 4-methoxyphenol, or 4-trifluoromethylphenol. The diol reactant 8 preferably is ethylene glycol, 1,3-propylene glycol, 1,2-benzenediol, 2,2'-biphenol, racemic 1,1'-bi-2-naphthol, (S)-1,1'-bi-2-naphthol, or (R)-1,1'-bi-2-naphthol.

Product 1 may be isolated from the reaction mixture according to procedures well-known to those skilled in the art. Examples of such procedures include extraction, filtration and crystallization. Product 1 may be purified if necessary using conventional methods, e.g., extraction, chromatography and crystallization processes.

The present invention also relates to complexes of the phosphine-phosphoramidite compounds of formula 1 with a catalytically-active metal. Such complexes are effective catalysts for promoting a large number of possible reactions employing a wide variety of reactants. Examples of possible reactions include asymmetric hydrogenations, asymmetric reductions, asymmetric hydroborations, asymmetric olefin isomerizations, asymmetric hydrosilations, asymmetric allylations, asymmetric conjugate additions and asymmetric organometallic additions.

The particular metal selected for complexation with the phosphine-phosphoramidite compounds of formula 1 depends on the desired reaction. The metal may be selected from Group VIII metals, with rhodium, ruthenium, and iridium being preferred. Although the complexes may be prepared and isolated prior to use, it is preferable to prepare a solution of the complex in situ from phosphine-phosphoramidite compound 1 and a metal pre-catalyst in a solvent, and use this solution directly in subsequent reactions. The relative amounts of phosphine-phosphoramidite compound 1 and catalytically-active metal employed typically provide a phosphorus:metal atomic ratio of about 1:1 to 5:1, preferably about 2:1 to 3:1.

The complexes of the present invention are generally prepared by mixing the metal precatalyst and phosphine-phosphoramidite compound 1 in an inert solvent chosen from aliphatic hydrocarbons, e.g., hexane, heptane, octane and the like; aromatic hydrocarbons, e.g., toluene, xylenes and the like; cyclic and acyclic ethers, e.g., tert-butyl methyl ether, diisopropyl ether, tetrahydrofuran (THF) and the like; lower alkanols, e.g., methanol, ethanol, n-propanol, isopropanol, n-butanol and the like; halogenated aliphatic or aromatic hydrocarbons, e.g., dichloromethane, tetrachloroethylene, chloroform, chlorobenzene and the like; dialkyl ketones, e.g., acetone, 2-butanone, 3-pentanone, methyl isopropyl ketone, methyl isobutyl ketone and the like, with preferred solvents being methanol, ethanol, dichloromethane, tetrahydrofuran, or acetone. The solvent may be, but is not required to be, the same as that used in subsequent reactions. The complexes are generally prepared at temperatures ranging between −50 and 50° C., preferably between 0 and 40° C. under an inert gas atmosphere.

The complexes of the phosphine-phosphoramidite compounds of formula 1 with a catalytically-active metal are especially useful in performing asymmetric hydrogenation reactions. Thus, the present invention includes a process for the hydrogenation of a hydrogenatable compound, which comprises contacting the hydrogenatable compound with hydrogen in the presence of a catalyst complex of a phosphine-phosphoramidite compound of formula 1 and a catalytically-active metal under hydrogenation conditions of temperature and pressure. For asymmetric hydrogenation reactions, the catalytically-active metal complexed with the compound of formula 1 preferably is rhodium, iridium, or ruthenium, and most preferably is rhodium. The amount of complex utilized in the hydrogenation process may vary between 0.00005 and 0.5 molar equivalents based on the hydrogenatable starting material, with more complex usually providing faster reaction rates. The reaction atmosphere is hydrogen, but may also contain other materials that are inert to the reaction conditions. The reaction can be run at atmospheric pressure or at elevated pressure, e.g., from about 0.5 to 200 bars gauge (barg). The reaction is run at a temperature which affords a reasonable rate of conversion, which can be as low as −50° C. but is usually between ambient temperature and the boiling point (or apparent boiling point at elevated pressure) of the lowest boiling component of the reaction mixture.

Our novel hydrogenation process normally is operated in the presence of an inert organic solvent such as aliphatic hydrocarbons, e.g., hexane, heptane, octane and the like; aromatic hydrocarbons, e.g., toluene, xylenes and the like; cyclic and acyclic ethers, e.g., tert-butyl methyl ether, diisopropyl ether, tetrahydrofuran (THF) and the like; lower alkanols, e.g., methanol, ethanol, n-propanol, isopropanol, n-butanol and the like; halogenated aliphatic or aromatic hydrocarbons, e.g., dichloromethane, tetrachloroethylene, chloroform, chlorobenzene and the like; dialkyl ketones, e.g., acetone, 2-butanone, 3-pentanone, methyl isopropyl ketone, methyl isobutyl ketone and the like; or polar aprotic solvents, e.g., dimethylformamide, dimethyl sulfoxide and the like.

A hydrogenation that is of particular interest to the pharmaceutical industry that may be performed using the inventive complexes is an asymmetric hydrogenation of a dehydroamino acid derivative ("enamide") to produce the corresponding amino acid derivative. Catalyst complexes of the phosphine-phosphoramidite compounds of formula 1 and a catalytically-active metal exhibit particularly high enantioselectivity for the asymmetric hydrogenation of enamides to produce the corresponding amino acid derivatives. Enamide compounds that may be hydrogenated in acordance with our invention are characterized by the molecular skeleton C=C(N—C=O)—C=O which, in accordance with our invention, are hydrogenated to the intended product in high enantioselectivity.

Thus, our novel hydrogenation process involves, for example, the preparation of a compound having formula 9

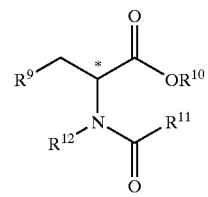

9 which comprises contacting an enamide having formula 10

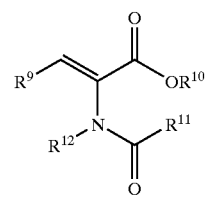

10 with hydrogen in the presence of a catalytic amount of a complex of a phosphine-phosphoramidite compound of formula 1 and a catalytically-active metal selected from rhodium, iridium, or ruthenium; wherein $R^9$, $R^{10}$, and $R^{12}$ are independently, hydrogen, substituted or unsubstituted, branched- or straight-chain $C_1$ to $C_{20}$ alkyl, substituted or unsubstituted $C_3$ to $C_8$ cycloalkyl, substituted or unsubstituted $C_6$ to $C_{20}$ carbocyclic aryl, or substituted or unsubstituted $C_4$ to $C_{20}$ heteroaryl having one to three heteroatoms wherein the heteroatoms are selected from sulfur, nitrogen, or oxygen; and $R^{11}$ is hydrogen, substituted or unsubstituted $C_1$ to $C_{20}$ alkyl, substituted or unsubstituted $C_1$ to $C_{20}$ alkoxy, substituted or unsubstituted $C_3$ to $C_8$ cycloalkyl, substituted or unsubstituted $C_3$ to $C_8$ cycloalkoxy, substituted or unsubstituted carbocyclic $C_6$ to $C_{20}$ aryl, substituted or unsubstituted carbocyclic $C_6$ to $C_{20}$ aryloxy, substituted or unsubstituted $C_4$ to $C_{20}$ heteroaryl having one to three heteroatoms wherein the heteroatoms are selected from sulfur, nitrogen, or oxygen or substituted or unsubstituted $C_4$ to $C_{20}$ heteroaryloxy having one to three heteroatoms wherein the heteroatoms are selected from sulfur, nitrogen, and oxygen. Examples of the substituents represented by $R^9$, $R^{10}$, R11 and $R^{12}$ are set forth above in the descriptions of R, $R^1$, $R^2$ and $R^3$.

The enamide starting material having formula 10 may be prepared using the methodology described by Schmidt et al., *Synthesis* 1984, 53–60; and Schmidt et al., *Synthesis* 1992, 487–490. The products having formula 9 generally are produced with very high enantioselectivity (>90% ee), with the particular enantiomer produced depending upon which enantiomer or diastereomer of phosphine-phosphoramidite compound 1 is used.

Another preferred embodiment of our novel hydrogenation process involves the preparation of a compound having formula 11

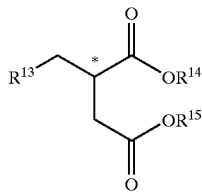

11 which comprises contacting an itaconate compound having formula 12

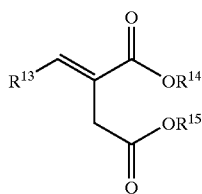

12 with hydrogen in the presence of a catalytic amount of a complex of a phosphine-phosphoramidite compound of formula 1 and a catalytically-active metal selected from rhodium, iridium, or ruthenium; wherein $R^{13}$, $R^{14}$, and $R^{15}$ are independently, hydrogen, substituted or unsubstituted, branched- or straight-chain $C_1$–$C_{20}$ alkyl, substituted or unsubstituted $C_3$–$C_8$ cycloalkyl, substituted or unsubstituted $C_6$–$C_{20}$ carbocyclic aryl, or substituted or unsubstituted $C_4$–$C_{20}$ heteroaryl having one to three heteroatoms wherein the heteroatoms are selected from sulfur, nitrogen, and oxygen. Itaconate starting materials of formula 12 are generally commercially available or can prepared by methods known to those skilled in the art. Compounds 11 typically are produced with very high enantioselectivity (>90% ee), with the particular enantiomer produced depending upon which enantiomer or diastereomer of phosphine-phosphoramidite compound 1 is used.

EXAMPLES

The novel compounds, complexes and processes provided by the present invention are further illustrated by the following examples. Unless specified otherwise, all percentages and ratios given in the examples are by mole.

Example 1

Preparation of (R)-N-diphenoxyphosphino-N-methyl-1-[(S)-2-(diphenylphosphino)ferrocenyl] ethylamine (2a)

Toluene (5 mL) was added to a 100-mL 3-necked flask which was cooled to below −70° C. in a dry ice-acetone bath. Phosphorus trichloride (0.26 mL; 3.0 mmol; 1.0 equiv) was added followed by triethylamine (0.50 mL; 3.6 mmol; 1.2 equiv). (R)-N-Methyl-1-[(S)-2-(diphenylphosphino) ferrocenyl]ethylamine (4a)(1.28 g; 3.0 mmol) dissolved in 15 mL of toluene was added dropwise such that the temperature remained below −50° C. The reaction mixture was stirred in dry ice-acetone for 1 hour, then allowed to warm to ambient temperature over 1 h and stirred at ambient temperature for 2 hours. The reaction mixture was cooled to below −70° C. and triethylamine (1.05 mL; 7.7 mmol; 2.5 equiv) was added followed by phenol (565 mg; 6.0 mmol; 2 equiv) in 10 mL of toluene. The reaction mixture was allowed to warm to ambient temperature overnight to completely consume 4a according to thin layer chromatography (tlc) analysis. Heptane (30 mL) was added and the reaction mixture was filtered through celite and eluted with heptane and ethyl acetate. The resulting filtrate was stripped and the residue was filtered through a pad of flash silica gel and eluted with 1:9 ethyl acetate:heptane with 5% added triethylamine to afford 1.52 g (79%) of 2a.

$^1$H NMR (CDCl$_3$) δ 7.60 (m, 2H); 7.37 (m, 3H); 7.21 (m, 2H); 7.1–6.8 (m, 11H); 6.62 (m, 2H); 5.13 (m, 1H); 4.492 (br s, 1H); 4.349 (m, 1H); 3.943 (m, 1H); 3.879 (s, 5H); 2.390 (d, 3H, J=4.94 Hz); 1.491 (d, 3H, J=6.87 Hz). FDMS: m/z 643.53 (M$^+$).

Example 2

Preparation of (R)-N-[bis(4-methoxyphenoxy) phosphino]-N-methyl-1-[(S)-2-(diphenylphosphino) ferrocenyl]ethylamine (2b)

Toluene (5 mL) was added to a 100-mL 3-necked flask which was cooled to <5° C. in an ice-water bath. Phosphorus trichloride (0.26 mL; 3.0 mmol; 1.0 equiv) was added followed by triethylamine (0.50 mL; 3.6 mmol; 1.2 equiv). (R)-N-Methyl-1-[(S)-2-(diphenylphosphino)ferrocenyl] ethylamine (4a)(1.28 g; 3.0 mmol) dissolved in 15 mL of toluene was added dropwise such that the temperature remained below 15° C. The reaction mixture was stirred in ice-water for 15 minutes, then allowed to warm to ambient temperature for 45 minutes. The reaction mixture was cooled to <5° C. in ice-water and triethylamine (1.05 mL; 7.7 mmol; 2.5 equiv) was added followed by 4-methoxyphenol (745 mg; 6.0 mmol; 2 equiv) in 10 mL of toluene at a rate such that the temperature remained below 15° C. The reaction mixture was allowed to warm to ambient temperature overnight to almost completely consume 4a according to tlc analysis. Heptane (30 mL) was added and the reaction mixture was filtered through celite and eluted with heptane and ethyl acetate. The resulting filtrate was stripped and the residue was filtered through a pad of flash silica gel and eluted with 1:9 ethyl acetate:heptane with 5% added triethylamine to afford 1.38 g (65%) of 2b.

$^1$H NMR (CDCl$_3$) δ 7.59 (m, 2H); 7.374 (m, 3H); 7.1–6.9 (m, 5H); 6.835 (d, 2H, J=8.52 Hz); 6.757 (dd, 2H, J=2.47, 6.87 Hz); 6.598 (d, 2H, J=9.07 Hz); 6.500 (dd, 2H, J=1.37, 9.07 Hz); 5.07 (m, 1H); 4.489 (br s, 1H); 4.347 (m, 1H); 3.950 (m, 1H); 3.866 (s, 5H); 3.757 (s, 3H); 3.710 (s, 3H); 2.376 (d, 3H, J=4.67 Hz); 1.493 (d, 3H, J=7.14 Hz). FDMS: m/z 703.01 (M$^+$).

Example 3

Preparation of (R)-N-[bis(4-trifluoromethylphenoxy)phosphino]-N-methyl-1-[(S)-2-(diphenylphosphino)ferrocenyl]ethylamine (2c)

Toluene (5 mL) was added to a 100-mL 3-necked flask which was cooled to <5° C. in an ice-water bath. Phosphorus trichloride (0.26 mL; 3.0 mmol; 1.0 equiv) was added followed by triethylamine (0.50 mL; 3.6 mmol; 1.2 equiv). (R)-N-Methyl-1-[(S)-2-(diphenylphosphino)ferrocenyl]ethylamine (4a)(1.28 g; 3.0 mmol) dissolved in 15 mL of toluene was added dropwise such that the temperature remained below 15° C. The reaction mixture was stirred in ice-water for 15 minutes, then allowed to warm to ambient temperature for 45 minutes. The reaction mixture was cooled to <5° C. in ice-water and triethylamine (1.05 mL; 7.7 mmol; 2.5 equiv) was added followed by 4-trifluoromethylphenol (973 mg; 6.0 mmol; 2 equiv) in 10 mL of toluene at a rate such that the temperature remained below 15° C. The reaction mixture was allowed to warm to ambient temperature overnight to almost completely consume 4a according to tlc analysis. Heptane (30 mL) was added and the reaction mixture was filtered through celite and eluted with heptane and ethyl acetate. The resulting filtrate was stripped and the residue was filtered through a pad of flash silica gel and eluted with 1:9 ethyl acetate:heptane with 5% added triethylamine to afford 1.29 g (55%) of 2c.

$^1$H NMR (CDCl$_3$) δ 7.58 (m, 2H); 7.502 (d, 2H, J=10.71 Hz); 7.4–7.3 (m, 5H); 7.1–6.9 (m, 5H); 6.87 (m, 2H); 6.667 (d, 2H, J=8.24 Hz); 5.17 (m, 1H); 4.502 (br s, 1H); 4.382 (m, 1H); 3.99 (m, 1H); 3.873 (s, 5H); 2.410 (d, 3H, J=4.95 Hz); 1.507 (d, 3H, J=6.87 Hz). FDMS: m/z 779.78 (M$^+$).

Example 4

Preparation of (R)-N-[(R),(R)-1,1'-binaphthyl-2,2'-dioxyphosphino]-N-methyl-1-[(S)-2-(diphenylphosphino)ferrocenyl]ethylamine (2d)

Toluene (5 mL) was added to a 100-mL 3-necked flask which was cooled to below –70° C. in a dry ice-acetone bath. Phosphorus trichloride (174 µL; 2.0 mmol; 1.0 equiv) was added followed by triethylamine (0.33 mL; 2.4 mmol; 1.2 equiv). (R)-N-1-[(S)-2-(diphenylphosphino)ferrocenyl]ethylamine (4a)(855 mg; 2.0 mmol) dissolved in 10 mL of toluene was added dropwise such that the temperature remained below –50° C. The reaction mixture was stirred in dry ice-acetone for 1 hour, then allowed to warm to ambient temperature over 1.5 hours and stirred for 2 hours at ambient temperature. The reaction mixture was cooled to below –70° C. and triethylamine (0.70 mL; 5.0 mmol; 2.5 equiv) was added followed by a warm toluene (15 mL) solution of (R)-1,1'-bi-2-naphthol (573 mg; 2.0 mmol; 1 equiv). This was washed in with 5 mL of toluene. The reaction mixture was allowed to warm to ambient temperature overnight to almost completely consume 4a according to tlc analysis. Heptane (30 mL) was added and the reaction mixture was filtered and eluted with heptane and ethyl acetate. The resulting filtrate was stripped and the residue was filtered through a pad of flash silica gel and eluted with 15:85 ethyl acetate:heptane with 5% added triethylamine to afford 1.06 g (71%) of 2d.

$^1$H NMR (CDCl$_3$) δ 7.9–7.1 (m, 21H); 6.738 (d, 1H, J=8.52 Hz); 5.33 (m, 1H); 4.462 (br s, 1H); 4.325 (m, 1H); 3.968 (s, 5H); 3.895 (m, 1H); 1.805 (d, 3H, J=7.14 Hz); 1.737 (d, 3H, J=3.57 Hz). FDMS: m/z 740.3 (M–H$^+$).

Example 5

Preparation of (R)-N-[(S),(S)-1,1'-binaphthyl-2,2'-dioxyphosphino]-N-methyl-1-[(S)-2-(diphenylphosphino)ferrocenyl]ethylamine (2e)

Toluene (5 mL) was added to a 100-mL 3-necked flask which was cooled to below –70° C. in a dry ice-acetone bath. Phosphorus trichloride (174 µL; 2.0 mmol; 1.0 equiv) was added followed by triethylamine (0.33 mL; 2.4 mmol; 1.2 equiv). (R)-N-Methyl-1-[(S)-2-(diphenylphosphino)ferrocenyl]ethylamine (4a)(855 mg; 2.0 mmol) dissolved in 10 mL of toluene was added dropwise such that the temperature remained below –50° C. The reaction mixture was stirred in dry ice-acetone for 1 hour, then allowed to warm to ambient temperature over 1.5 hours and stirred for 2 hours at ambient temperature. The reaction mixture was cooled to below –70° C. and triethylamine (0.70 mL; 5.0 mmol; 2.5 equiv) was added followed by a warm toluene (15 mL) solution of (S)-1,1'-bi-2-naphthol (573 mg; 2.0 mmol; 1 equiv). This was washed in with 5 mL of toluene. The reaction mixture was allowed to warm to ambient temperature overnight to almost completely consume 4a according to tlc analysis. Heptane (30 mL) was added and the reaction mixture was filtered and eluted with heptane and ethyl acetate. The resulting filtrate was stripped and the residue was filtered through a pad of flash silica gel and eluted with 1:9 ethyl acetate:heptane with 5% added triethylamine to afford 0.93 g (63%) of 2e. This material was triturated with hot toluene, diluted with heptane, cooled to ambient temperature, and filtered. The precipitate was washed with 1:4 toluene:heptane and dried to afford 752 mg (51%) of 2e.

$^1$H NMR (CDCl$_3$) δ 7.9–7.1 (m, 21H); 6.056 (d, 1H; I=9.07 Hz); 5.19 (m, 1H); 4.519 (br s, 1H); 4.402 (m, 1H); 4.112 (m, 1H); 3.891 (s, 5H); 1.932 (d, 3H, I=3.57 Hz); 1.694 (d, 3H, I=6.87 Hz). FDMS: m/z 740.3 (M–H$^+$).

Example 6

Preparation of N-Acetyl L-phenylalanine Methyl Ester (S-9a) Using the Rhodium Complex of Ligand 2a Enamide 10a (R$^9$=phenyl, R$^{10}$=R$^{11}$=methyl, R$^{12}$=H) (110 mg; 0.5 mmol) was dissolved in a reaction vessel in anhydrous tetrahydrofuran (THF, 4.0 mL) and degassed with argon for 15 minutes. Bis(1,5-cyclooctadiene)rhodium trifluoromethanesulfonate (2.3 mg; 5 µmol; 0.01 equiv) and ligand 2a from Example 1 (3.9 mg; 6 µmol; 0.012 equiv) were combined and argon-degassed anhydrous THF (1.0 mL) was added. This solution was stirred at 25° C. under argon for 15 minutes and then added to the solution of 10a. The resulting solution was then flushed with hydrogen and pressurized to 0.69–1.38 bars gauge (10–20 pounds per square inch gauge-psig) hydrogen. The reaction mixture was stirred for 6 hours to afford 99.7% conversion to amino acid derivative S-9a (R$^9$=phenyl, R$^{10}$=R$^{12}$=methyl, R$^{13}$=H) with 92.6% ee as determined by chiral GC analysis.

$^1$H NMR (CD$_3$OD, 400 MHz) δ 7.28–7.16 (m, 5H), 4.64–4.61 (m, 1H), 3.65 (s, 3H), 3.13–3.08 (dd, 1H, J=5.5, 13.9 Hz), 2.94–2.88 (dd, 1H, J=8.9, 13.9 Hz), 1.87 (s, 3H). Chiral GC conditions: Chirasil L-Valine [Varian] 25 m×0.25 mm ID, film thickness 0.12 µm, 160° C. 9 min, 160–185° C. 70° C./min, 185° C. 5 min, 15 psig He. t$_R$(R-9a) 7.77 min, t$_R$(S-9a) 8.29 min, t$_R$(10a) 13.24 min.

Example 7

Preparation of N-Acetyl L-phenylalanine (S-9b) Using the Rhodium Complex of Ligand 2a Enamide 10b (R$^9$=phenyl, R$^{11}$=methyl, R$^{10}$=R$^{12}$=H) (102 mg; 0.5 mmol) was dissolved in a reaction vessel in anhydrous THF (4.0 mL) and degassed with argon for 15 minutes. Bis(1,5-cyclooctadiene)rhodium trifluoromethanesulfonate (2.3 mg; 5 µmol; 0.01 equiv) and ligand 2a from Example 1 (3.9 mg; 6 µmol; 0.012 equiv) were combined and argon-degassed anhydrous THF (1.0 mL) was added. This solution was stirred at 25° C. under argon for 15 minutes and then added to the solution of 10b. The resulting solution was then flushed with hydrogen and pressurized to 0.69–1.38 bars gauge (10–20 psig) hydrogen. The reaction mixture was stirred for 6 hours, at which point a sample (0.024 mmol) was converted to the methyl ester 9a by the action of trimethylsilyldiazomethane (2.0 M in hexane; 60 µL; 0.12 mmol; 5 equiv) by stirring in methanol (1 mL) for 30 min. After acetic acid quench, the sample was analyzed directly to indicate 97.4% conversion to amino acid derivative S-9b ($R^9$=phenyl, $R^{11}$=methyl, $R^{10}$=$R^{12}$=H) with 97.0% ee as determined by chiral GC analysis.

Example 8

Preparation of N-Acetyl L-phenylalanine Methyl Ester (S-9a) Using the Rhodium Complex of Ligand 2b Enamide 10a ($R^9$=phenyl, $R^{10}$=$R^{11}$=methyl, $R^{12}$=H) (110 mg; 0.5 mmol) was dissolved in a reaction vessel in anhydrous THF (5.0 mL) and degassed with argon for 15 minutes. Bis(1,5-cyclooctadiene)rhodium trifluoromethanesulfonate (2.3 mg; 5 µmol; 0.01 equiv) and ligand 2b from Example 2 (4.2 mg; 6 µmol; 0.012 equiv) were combined and argon-degassed anhydrous THF (0.75 mL) was added. This solution was stirred at 25° C. under argon for 15 minutes and then added to the solution of 10a. The resulting solution was then flushed with hydrogen and pressurized to 0.69–1.38 bars gauge (10–20 psig) hydrogen. The reaction mixture was stirred for 6 hours to afford 100% conversion to amino acid derivative S-9a ($R^9$=phenyl, $R^{10}$=$R^{12}$=methyl, $R^{13}$=H) with 95.2% ee as determined by chiral GC analysis.

Example 9

Preparation of N-Acetyl L-phenylalanine (S-9b) Using the Rhodium Complex of Ligand 2b Enamide 10b ($R^9$=phenyl, $R^{11}$=methyl, $R^{10}$=$R^{12}$=H) (102 mg; 0.5 mmol) was dissolved in a reaction vessel in anhydrous THF (5.0 mL) and degassed with argon for 15 minutes. Bis(1,5-cyclooctadiene)rhodium trifluoromethanesulfonate (2.3 mg; 5 µmol; 0.01 equiv) and ligand 2b from Example 2 (4.2 mg; 6 µmol; 0.012 equiv) were combined and argon-degassed anhydrous THF (0.75 mL) was added. This solution was stirred at 25° C. under argon for 15 minutes and then added to the solution of 10b. The resulting solution was then flushed with hydrogen and pressurized to 0.69–1.38 bars gauge (10–20 psig) hydrogen. The reaction mixture was stirred for 6 hours, at which point a sample (0.024 mmol) was converted to the methyl ester 9a by the action of trimethylsilyldiazomethane (2.0 M in hexane; 60 µL; 0.12 mmol; 5 equiv) by stirring in methanol (1 mL) for 30 min. After acetic acid quench, the sample was analyzed directly to indicate 100% conversion to amino acid derivative S-9b ($R^9$=phenyl, $R^{11}$=methyl, $R^{10}$=$R^{12}$=H) with 98.0% ee as determined by chiral GC analysis.

Example 10

Preparation of N-Acetyl L-phenylalanine Methyl Ester (S-9a) Using the Rhodium Complex of Ligand 2c Enamide 10a ($R^9$=phenyl, $R^{10}$=$R^{11}$=methyl, $R^{12}$=H) (110 mg; 0.5 mmol) was dissolved in a reaction vessel in anhydrous THF (5.0 mL) and degassed with argon for 15 minutes. Bis(1,5-cyclooctadiene)rhodium trifluoromethanesulfonate (2.3 mg; 5 µmol; 0.01 equiv) and ligand 2c from Example 3 (4.7 mg; 6 µmol; 0.012 equiv) were combined and argon-degassed anhydrous THF (0.50 mL) was added. This solution was stirred at 25° C. under argon for 15 minutes and then added to the solution of 10a. The resulting solution was then flushed with hydrogen and pressurized to 0.69–1.38 bars gauge (10–20 psig) hydrogen. The reaction mixture was stirred for 6 hours to afford 100% conversion to amino acid derivative S-9a ($R^9$=phenyl, $R^{10}$=$R^{12}$=methyl, $R^{13}$=H) with 91.0% ee as determined by chiral GC analysis.

Example 11

Preparation of N-Acetyl L-phenylalanine (S-9b) Using the Rhodium Complex of Ligand 2c Enamide 10b ($R^9$=phenyl, $R^{11}$=methyl, $R^{10}$=$R^{12}$=H) (102 mg; 0.5 mmol) was dissolved in a reaction vessel in anhydrous THF (5.0 mL) and degassed with argon for 15 minutes. Bis(1,5-cyclooctadiene)rhodium trifluoromethanesulfonate (2.3 mg; 5 µmol; 0.01 equiv) and ligand 2c from Example 3 (4.7 mg; 6 µmol; 0.012 equiv) were combined and argon-degassed anhydrous THF (0.50 mL) was added. This solution was stirred at 25° C. under argon for 15 minutes and then added to the solution of 10b. The resulting solution was then flushed with hydrogen and pressurized to 0.69–1.38 bars gauge (10–20 psig) hydrogen. The reaction mixture was stirred for 6 hours, at which point a sample (0.024 mmol) was converted to the methyl ester 9a by the action of trimethylsilyldiazomethane (2.0 M in hexane; 60 µL; 0.12 mmol; 5 equiv) by stirring in methanol (1 mL) for 30 min. After acetic acid quench, the sample was analyzed directly to indicate 100% conversion to amino acid derivative S-9b ($R^9$=phenyl, $R^{11}$=methyl, $R^{10}$=$R^{12}$=H) with 97.2% ee as determined by chiral GC analysis.

Example 12

Preparation of N-Acetyl L-alanine (S-9c) Using the Rhodium Complex of Ligand 2c

Enamide 10c ($R^9$=$R^{10}$=$R^{12}$=H, $R^{11}$=methyl) (65 mg; 0.5 mmol) was dissolved in a reaction vessel in anhydrous THF (5.0 mL) and degassed with argon for 15 minutes. Bis(1,5-cyclooctadiene)rhodium trifluoromethanesulfonate (2.3 mg; 5 µmol; 0.01 equiv) and ligand 2c from Example 3 (4.7 mg; 6 µmol; 0.012 equiv) were combined and argon-degassed anhydrous THF (0.50 mL) was added. This solution was stirred at 25° C. under argon for 15 minutes and then added to the solution of 10c. The resulting solution was then flushed with hydrogen and pressurized to 0.69–1.38 bars gauge (10–20 psig) hydrogen. The reaction mixture was stirred for 6 hours, at which point a sample (0.024 mmol) was converted to the methyl ester by the action of trimethylsilyldiazomethane (2.0 M in hexane; 60 µL; 0.12 mmol; 5 equiv) by stirring in methanol (1 mL) for 30 min. After acetic acid quench, the sample was analyzed directly to indicate 33.0% conversion to amino acid derivative S-9c ($R^9$=$R^{10}$=$R^{12}$=H, $R^{11}$=methyl) with 90.0% ee as determined by chiral GC analysis.

Chiral GC conditions: Cyclosil-[J&W Scientific] 30 m×0.25 mm ID, 0.25 µm film thickness, 40–100° C. 70° C./min, 100° C. 15 min, 100–170° C. 15° C./min, 170° C. 7 min, 6 psig He 6 min, 6–20 psig He 80 psig/min, 20 psig 22 min. $t_R$(R-N-acetylalanine methyl ester) 19.36 min, $t_R$(S-N-acetylalanine methyl ester) 19.12 min, $t_R$(methyl 2-acetamidoacrylate) 17.91 min.

Example 13

Preparation of N-Acetyl L-phenylalanine Methyl Ester (S-9a) Using the Rhodium Complex of Ligand 2d Enamide 10a ($R^9$=phenyl, $R^{10}$=$R^{11}$=methyl, $R^{12}$=H) (110 mg; 0.5 mmol) was dissolved in a reaction vessel in anhydrous THF (5.0 mL) and degassed with argon for 15 minutes. Bis(1,5-cyclooctadiene)rhodium trifluoromethanesulfonate (2.3 mg; 5 µmol; 0.01 equiv) and ligand 2d from Example 4 (4.4 mg; 6 µmol; 0.012 equiv) were combined and argon-degassed anhydrous THF (0.50 mL) was added. This solution was stirred at 25° C. under argon for 15 minutes and then added to the solution of 10a. The resulting solution was then flushed with hydrogen and pressurized to 0.69–1.38 bars gauge (10–20 psig) hydrogen. The reaction mixture was stirred for 6 hours to afford 34.1% conversion to amino acid derivative S-9a ($R^9$=phenyl, $R^{10}$=$R^{12}$=methyl, $R^{13}$=H) with 99.1% ee as determined by chiral GC analysis.

Example 14

Preparation of N-Acetyl L-phenylalanine (S-9b) Using the Rhodium complex of Ligand 2d Enamide 10b ($R^9$=phenyl, $R^{11}$=methyl, $R^{10}$=$R^{12}$=H) (102 mg; 0.5 mmol) was dissolved in a reaction vessel in anhydrous THF (5.0 mL) and degassed with argon for 15 minutes. Bis(1,5-cyclooctadiene)rhodium trifluoromethanesulfonate (2.3 mg; 5 µmol; 0.01 equiv) and ligand 2d from Example 4 (4.4 mg; 6 µmol; 0.012 equiv) were combined and argon-degassed anhydrous tetrahydrofuran (THF, 0.50 mL) was added. This solution was stirred at 25° C. under argon for 15 minutes and then added to the solution of 10b. The resulting solution was then flushed with hydrogen and pressurized to 0.69–1.38 bars gauge (10–20 psig) hydrogen. The reaction mixture was stirred for 6 hours, at which point a sample (0.024 mmol) was converted to the methyl ester 9a by the action of trimethylsilyldiazomethane (2.0 M in hexane; 60 µL; 0.12 mmol; 5 equiv) by stirring in methanol (1 mL) for 30 min. After acetic acid quench, the sample was analyzed directly to indicate 98.8% conversion to amino acid derivative S-9b ($R^9$=phenyl, $R^{11}$=methyl, $R^{10}$=$R^{12}$=H) with 99.9% ee as determined by chiral GC analysis.

Example 15

Preparation of N-Acetyl L-phenylalanine (S-9b) Using the Rhodium Complex of Ligand 2d at Substrate:Catalyst Ratio of 2500:1

Enamide 10b ($R^9$=phenyl, $R^{11}$=methyl, $R^{10}$=$R^{12}$=H) (2.05 g; 10.0 mmol) was dissolved in argon-degassed methanol (12.3 mL) in a pressure bottle. A pressure head was attached and the bottle was evacuated and filled with helium ten times. In a separate flask were combined bis(1,5-cyclooctadiene)rhodium trifluoromethanesulfonate (5.6 mg; 0.012 mmol) and ligand 2d from Example 4 (10.7 mg; 0.0144 mol; 0.012 equiv based on rhodium). The flask was purged with argon for 5 min and argon-degassed methanol (3.0 mL) was added. This was stirred at 25° C. under argon for 15 minutes to afford a 4 mM solution of catalyst. To the solution of 10b in the pressure vessel was added 1.0 mL (0.004 mmol; 0.0004 equiv; S:C 2500:1) of the catalyst solution and the resulting mixture was evacuated and filled with helium ten times. The mixture was evacuated and filled with hydrogen five times, then pressurized to 2.76 barg (40 psig) with hydrogen, sealed, and stirred vigorously. The course of the reaction was followed by the pressure drop within the vessel. Hydrogen consumption had ceased within 1.9 h, and the vessel was evacuated and filled with helium five times. A portion of the reaction mixture (31 µL; 0.024 mmol) was converted to the methyl ester 9a by the action of trimethylsilyldiazomethane (2.0 M in hexane; 60 µL; 0.12 mmol; 5 equiv) by stirring in methanol (1 mL) for 30 min. After acetic acid quench, the sample was analyzed directly to indicate 99.5% conversion to amino acid derivative S-9b ($R^9$=phenyl, $R^{11}$=methyl, $R^{10}$=$R^{12}$=H) with 99.82% ee as determined by chiral GC analysis. Analysis of the pressure vs. time data by correlation of the pressure drop with the extent of reaction (using the final conversion and pressure numbers) and adjustment for the amount of catalyst present indicated a catalyst turnover frequency at the initial stages of the reaction of 6000 turnovers per hour. The remainder of the reaction mixture was stripped to afford 2.05 g (99%) of S-9b ($R^9$=phenyl, $R^{11}$=methyl, $R^{10}$=$R^{12}$=H).

Example 16

Preparation of N-Acetyl L-4-chlorophenylalanine Methyl Ester (S-9d) Using the Rhodium Complex of Ligand 2d Enamide 10d ($R^9$=4-chlorophenyl, $R^{10}$=$R^{11}$=methyl, $R^{12}$=H) (126 mg; 0.5 mmol) was dissolved in a reaction vessel in anhydrous THF (5.0 mL) and degassed with argon for 15 minutes. Bis(1,5-cyclooctadiene)rhodium trifluoromethanesulfonate (2.3 mg; 5 µmol; 0.01 equiv) and ligand 2d from Example 4 (4.4 mg; 6 µmol; 0.012 equiv) were combined and argon-degassed anhydrous THF (0.50 mL) was added. This solution was stirred at 25° C. under argon for 15 minutes and then added to the solution of 10d. The resulting solution was then flushed with hydrogen and pressurized to 0.69–1.38 bars gauge (10–20 psig) hydrogen. The reaction mixture was stirred for 6 hours to afford 86.0% conversion to amino acid derivative S-9d ($R^9$=4-chlorophenyl, $R^{10}$=$R^{12}$=methyl, $R^{13}$=H) with 99.1% ee as determined by chiral GC analysis.

$^1$H NMR (CD$_3$OD, 600 MHz) δ7.27–7.25 (d, 2H, J=8.7 Hz), 7.18–7.16 (d, 2H, I=8.7 Hz), 4.64–4.62 (dd, 1H, J=5.5, 9.2 Hz), 3.70 (s, 1H), 3.67 (s, 3H), 3.13–3.09 (dd, 1H, J=5.5, 13.7 Hz), 2.93–2.89 (dd, 1H, J=9.2, 13.9 Hz), 1.88 (s, 3H). Chiral GC conditions: Chirasil L-Valine [Varian] 25 m×0.25 mm ID, film thickness 0.12 µm, 175° C. 25 min, 20 psig He, $t_R$(R-9d) 7.29 min, $t_R$(S-9d) 7.76 min, $t_R$(10d) 15.72 min.

Example 17

Preparation of N-Acetyl L-2-naphthylalanine Methyl Ester (S-9e) Using the Rhodium Complex of Ligand 2d Enamide 10e ($R^9$=2-naphthyl, $R^{10}$=$R^{11}$=methyl, $R^{12}$=H) (135 mg; 0.5 mmol) was dissolved in a reaction vessel in anhydrous THF (5.0 mL) and degassed with argon for 15 minutes. Bis(1,5-cyclooctadiene)rhodium trifluoromethanesulfonate (2.3 mg; 5 µmol; 0.01 equiv) and ligand 2d from Example 4 (4.4 mg; 6 µmol; 0.012 equiv) were combined and argon-degassed anhydrous THF (0.50 mL) was added. This solution was stirred at 25° C. under argon for 15 minutes and then added to the solution of 10e. The resulting solution was then flushed with hydrogen and pressurized to 0.69–1.38 bars gauge (10–20 psig) hydrogen. The reaction mixture was stirred for 6 hours to afford 99.7% conversion to amino acid derivative S-9e ($R^9$=2-naphthyl, $R^{10}$=$R^{12}$=methyl, $R^{13}$=H) with 97.7% ee as determined by chiral GC analysis.

¹H NMR (CDCl₃, 300 MHz) δ 7.85–7.75 (m, 3H); 7.553 (s, 1H); 7.47 (m, 2H); 7.218 (d, 1H, J=8.52 Hz); 6.01 (br s, 1H); 4.966 (q, 1H, J=6.04 Hz); 3.727 (s, 3H); 3.314 (dd, 1H, J=5.77, 13.74 Hz); 3.244 (dd, 1H, J=6.04, 14.01 Hz); 1.973 (s, 3H). Chiral GC conditions: Chirasil L-Valine [Varian] 25 m×0.25 mm ID, film thickness 0.12 μm, 185° C. 30 min, 15 psig He, $t_R$(R-9e) 22.02 min, $t_R$(S-9e) 23.26 min.

Example 18

Preparation of R-2-methylsuccinic Acid (S-11a) Using the Rhodium Complex of Ligand 2d Itaconic acid (12a, $R^{13}=R^{14}=R^{15}=H$) (65 mg; 0.5 mmol) was dissolved in a reaction vessel in anhydrous methanol (5.0 mL) and degassed with argon for 15 minutes. Bis(1,5-cyclooctadiene)rhodium trifluoromethanesulfonate (2.3 mg; 5 μmol; 0.01 equiv) and ligand 2d from Example 4 (4.4 mg; 6 μmol; 0.012 equiv) were combined and argon-degassed anhydrous methanol (0.50 mL) was added. This solution was stirred at 25° C. under argon for 15 minutes and then added to the solution of 12a. The resulting solution was then flushed with hydrogen and pressurized to 0.69–1.38 bars gauge (10–20 psig) hydrogen. The reaction mixture was stirred for 6 hours at which point a sample (0.024 mmol) was converted to the dimethyl ester 11b by the action of trimethylsilyldiazomethane (2.0 M in hexane; 120 μL; 0.12 mmol; 5 equiv) by stirring in methanol (1 mL) for 30 min. After acetic acid quench, the sample was analyzed directly to indicate 99.2% conversion to R-2-methylsuccinic acid (R-11a $R^{13}=R^{14}=R^{15}=H$) with 95.7% ee as determined by chiral GC analysis.

Chiral GC of 11b ($R^{13}=H$, $R^{14}=R^{15}=$methyl) [Cyclosil-B, J&W Scientific, 30 m×0.25 mm ID, film thickness 0.25 μm, 90° C. isothermal, 15 psig He]: $t_R$(R-11b) 17.36 min, $t_R$(S-11b) 17.82 min, $t_R$(12b) 23.16 min.

Example 19

Preparation of R-2-methylsuccinic acid (S-11a) Using the Rhodium Complex of Ligand 2e Itaconic acid (12a, $R^{13}=R^{14}=R^{15}=H$) (65 mg; 0.5 mmol) was dissolved in a reaction vessel in anhydrous methanol (5.0 mL) and degassed with argon for 15 minutes. Bis(1,5-cyclooctadiene)rhodium trifluoromethanesulfonate (2.3 mg; 5 μmol; 0.01 equiv) and ligand 2e from Example 5 (4.4 mg; 6 μmol; 0.012 equiv) were combined and argon-degassed anhydrous methanol (0.50 mL) was added. This solution was stirred at 25° C. under argon for 15 minutes and then added to the solution of 12a. The resulting solution was then flushed with hydrogen and pressurized to 0.69–1.38 bars gauge (10–20 psig) hydrogen. The reaction mixture was stirred for 6 hours at which point a sample (0.024 mmol) was converted to the dimethyl ester 11b by the action of trimethylsilyldiazomethane (2.0 M in hexane; 120 μL; 0.12 mmol; 5 equiv) by stirring in methanol (1 mL) for 30 min. After acetic acid quench, the sample was analyzed directly to indicate 100% conversion to R-2-methylsuccinic acid (R-11a $R^{13}=R^{14}=R^{15}=H$) with 92.6% ee as determined by chiral GC analysis.

The invention has been described in detail with particular reference to preferred embodiments thereof, but it will be understood that variations and modifications can be effected within the spirit and scope of the invention.

I claim:

1. A compound having the formula 1:

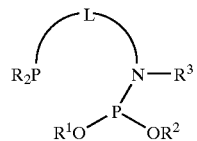

wherein

R and $R^3$ are substituted or unsubstituted, branched- or straight-chain $C_1$–$C_{20}$ alkyl, substituted or unsubstituted $C_3$–$C_8$ cycloalkyl, substituted or unsubstituted $C_6$–$C_{20}$ carbocyclic aryl, or substituted or unsubstituted $C_4$–$C_{20}$ heteroaryl having one to three heteroatoms wherein the heteroatoms are selected from sulfur, nitrogen, and oxygen;

$R^1$ and $R^2$ are, independently, achiral or substantially enantiomerically pure, substituted or unsubstituted, branched- or straight-chain $C_1$–$C_{20}$ alkyl, substituted or unsubstituted $C_3$–$C_8$ cycloalkyl, substituted or unsubstituted $C_6$–$C_{20}$ carbocylic aryl, substituted or unsubstituted $C_4$–$C_{20}$ heteroaryl having one to three heteroatoms wherein the heteroatoms are selected from sulfur, nitrogen, and oxygen, or $R^1$ and $R^2$ collectively represent a substituted or unsubstituted achiral, chiral and racemic, or substantially enantiomerically pure divalent alkylene, cycloalkylene or arylene radical wherein the chain of carbon atoms in the main chain that joins the amidite oxygen atoms in formula 1 contains 2 to about 8 carbon atoms;

L is a divalent chiral radical selected from substituted or unsubstituted, branched- or straight-chain $C_1$–$C_{20}$ alkylene, substituted or unsubstituted $C_3$–$C_8$ cycloalkylene, substituted or unsubstituted $C_6$–$C_{20}$ carbocyclic arylene, substituted or unsubstituted $C_4$–$C_{20}$ heteroarylene having one to three heteroatoms wherein the heteroatoms are selected from sulfur, nitrogen, and oxygen, or substituted or unsubstituted metallocenylmethylene, wherein L is substantially enantiomerically pure.

2. A compound according to claim 1 having formula 2 or 3:

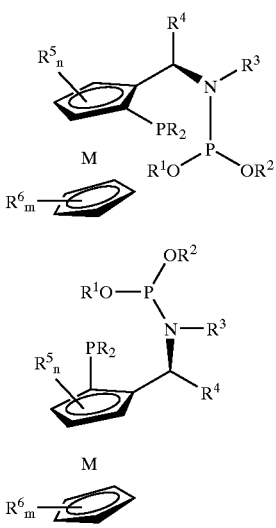

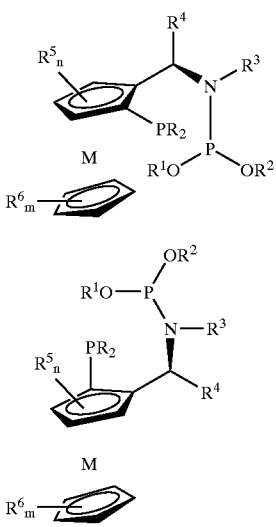

wherein
  $R^4$, $R^5$, and $R^6$ are, independently, hydrogen, substituted or unsubstituted, branched- or straight-chain $C_1$–$C_{20}$ alkyl, substituted or unsubstituted $C_3$–$C_8$ cycloalkyl, substituted or unsubstituted $C_6$–$C_{20}$ carbocyclic aryl, or substituted or unsubstituted $C_4$–$C_{20}$ heteroaryl having one to three heteroatoms wherein the heteroatoms are selected from sulfur, nitrogen, and oxygen;
  n is 0 to 3;
  m is 0 to 5; and
  M is a metal of Groups IVB, VB, VIB, VIIB and VIII.

3. A compound according to claim 1 having formulas 2 or 3:

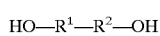

wherein
  R is aryl; $R^1$ and $R^2$ individually are aryl or collectively are 1,2-ethanediyl, 1,3-propanediyl, 1,2-benzenediyl, 2,2'-biphenyldiyl, racemic 1,1'-binaphthyl-2,2'-diyl, (R,R) 1,1'-binaphthyl-2,2'-diyl, or (S,S)-1,1'-binaphthyl-2,2'-diyl; $R^3$ is hydrogen, $C_1$–$C_6$ alkyl, or aryl; $R^4$ is hydrogen or $C_1$–$C_6$ alkyl; $R^5$ and $R^6$ are hydrogen;
  n is 0;
  m is 0; and
  M is iron.

4. Process for the preparation of a compound of formula 1 in claim 1 which comprises:
  (1) contacting an amine having the formula 4

$$R_2P\text{—}L\text{—}NHR^3 \qquad 4$$

with phosphorus trihalide $PX_3$ in an inert solvent to obtain an intermediate dihalide having formula 5

$$R_2P\text{—}L\text{—}N(R^3)P\text{—}X_2 \qquad 5$$

and
  (2) contacting intermediate dihalide 5 with one or more hydroxyl-containing reactants having formulas 6, 7 or 8:

$$R^1\text{—}OH, \qquad 6$$

$$R^2\text{—}OH \text{ or} \qquad 7$$

$$HO\text{—}R^1\text{—}R^2\text{—}OH \qquad 8$$

wherein
  X is halogen.

5. Process according to claim 4 wherein the process is carried out in the presence of an inert organic solvent; step (1) is carried out at a temperature between about −100° C. and the boiling point of the solvent and in the presence of an acid acceptor; and step (2) is carried out at a temperature between about −100° C. and the boiling point of the solvent.

6. Process according to claim 4 wherein the process is carried out in an inert organic solvent selected from diethyl ether, diisopropyl ether, tert-butyl methyl ether, tetrahydrofuran, benzene, toluene, xylene, hexane, heptane, cyclohexane or a mixture of any two or more thereof; step (1) of the process is carried out at a temperature of about −80° to 40° C. and in the presence of an acid acceptor selected from $C_3$–$C_{15}$ tertiary amines or pyridines; and step (2) is carried out at a temperature of about −80° to 40° C., and, optionally, in the presence of an acid acceptor selected from $C_3$–$C_{15}$ tertiary amines or pyridines.

7. Process according to claim 6 wherein the process is carried out in toluene and in the presence of triethylamine and wherein hydroxyl-containing reactants are phenol, 4-methoxyphenol, 4-trifluoromethylphenol, ethylene glycol, 1,3-propylene glycol, o-hydroquinone, 2,2'-biphenol, racemic 1,1'-bi-2-naphthol, (S)-1,1'-bi-2-naphthol, (R)-1,1'-bi-2-naphthol or a mixture thereof.

8. A metal complex compound comprising a compound of formula 1 defined in claim 1 and a catalytically-active metal selected from Group VIII metals.

9. A metal complex compound comprising a compound of formula 2 or 3 defined in claim 2 and rhodium, iridium or ruthenium.

10. A metal complex compound comprising a compound formula 2 or 3 defined in claim 3 and rhodium.

11. Process for hydrogenating a hydrogenatable compound which comprises contacting the hydrogenatable compound with hydrogen in the presence of an inert 10 organic solvent and the catalyst complex compound of claim 8.

12. Process for the preparation of a compound having formula 9

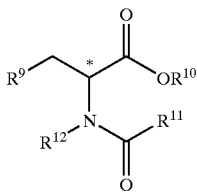

which comprises contacting an enamide having formula 10

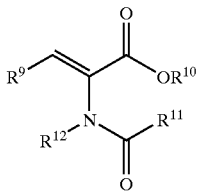

with hydrogen in the presence of a catalytic amount of a complex compound of claim 9 and in an inert organic solvent to form a reaction mixture, under pressure of about 0.5 to 200 bars gauge and a temperature between ambient temperature and the boiling point of the lowest boiling component of the reaction mixture, wherein $R^9$, R10, and $R^{12}$ are, independently, hydrogen, substituted or unsubstituted, branched- or straight-chain $C_1$ to $C_{20}$ alkyl, substituted or unsubstituted $C_3$ to $C_8$ cycloalkyl, substituted or unsubstituted $C_6$ to $C_{20}$ carbocyclic aryl, or substituted or unsubstituted $C_4$ to $C_{20}$ heteroaryl having one to three heteroatoms wherein the heteroatoms are selected from sulfur, nitrogen, or oxygen; and $R^{11}$ is hydrogen, substituted or unsubstituted $C_1$ to $C_{20}$ alkyl, substituted or unsubstituted $C_1$ to $C_{20}$ alkoxy, substituted or unsubstituted $C_3$ to $C_8$ cycloalkyl, substituted or unsubstituted $C_3$ to $C_8$ cycloalkoxy, substituted or unsubstituted carbocyclic $C_6$ to $C_{20}$ aryl, substituted or unsubstituted carbocyclic $C_6$ to $C_{20}$ aryloxy, substituted or unsubstituted $C_4$ to $C_{20}$ heteroaryl having one to three heteroatoms wherein the heteroatoms are selected from sulfur, nitrogen, or oxygen or substituted or unsubstituted $C_4$ to $C_{20}$ heteroaryloxy having one to three heteroatoms wherein the heteroatoms are selected from sulfur, nitrogen, and oxygen.

13. Process according to claim 12 wherein the complex compound comprises rhodium and a compound of formula 2 or 3 wherein R is aryl; $R^1$ and $R^2$ individually are aryl or collectively are 1,2-ethanediyl, 1,3-propanediyl, 1,2-benzenediyl, 2,2'-biphenyldiyl, racemic 1,1'-binaphthyl-2,2'-diyl, (R,R)-1,1'-binaphthyl-2,2'-diyl, or (S,S)-1,1'-binaphthyl-2,2'-diyl; $R^3$ is hydrogen, $C_1$–$C_6$ alkyl, or aryl; $R^4$ is hydrogen or $C_1$–$C_6$ alkyl; $R^5$ and $R^6$ are hydrogen; n is 0; m is 0; and M is iron.

14. Process for the preparation of a compound having formula 11

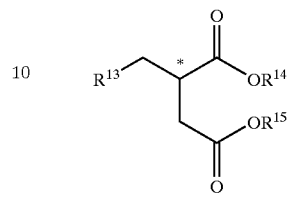

which comprises contacting an itaconate compound having formula 12

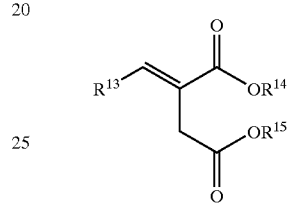

with hydrogen in the presence of a catalytic amount of a complex compound of claim 9 and in an inert organic solvent to form a reaction mixture, under a pressure of about 0.5 to 200 bars gauge and a temperature between ambient temperature and the boiling point of the lowest boiling component of the reaction mixture, wherein $R^{13}$, $R^{14}$, and $R^{15}$ are, independently, hydrogen, substituted or unsubstituted, branched- or straight-chain $C_1$–$C_{20}$ alkyl, substituted or unsubstituted $C_3$–$C_8$ cycloalkyl, substituted or unsubstituted $C_6$–$C_{20}$ carbocyclic aryl, or substituted or unsubstituted $C_4$–$C_{20}$ heteroaryl having one to three heteroatoms wherein the heteroatoms are selected from sulfur, nitrogen, and oxygen.

15. Process according to claim 14 wherein the complex compound comprises rhodium and a compound of formula 2 or 3 wherein R is aryl; $R^1$ and $R^2$ individually are aryl or collectively are 1,2-ethanediyl, 1,3-propanediyl, 1,2-benzenediyl, 2,2'-biphenyldiyl, racemic 1,1'-binaphthyl-2,2'-diyl, (R,R)-1,1'-binaphthyl-2,2'-diyl, or (S,S)-1,1'-binaphthyl-2,2'-diyl; $R^3$ is hydrogen, $C_1$–$C_6$ alkyl, or aryl; $R^4$ is hydrogen or $C_1$–$C_6$ alkyl; $R^5$ and $R^6$ are hydrogen; n is 0; m is 0; and M is iron.

* * * * *

UNITED STATES PATENT AND TRADEMARK OFFICE
CERTIFICATE OF CORRECTION

PATENT NO. : 6,906,212 B1 Page 1 of 1
DATED : June 14, 2005
INVENTOR(S) : Boaz

It is certified that error appears in the above-identified patent and that said Letters Patent is hereby corrected as shown below:

Column 20,
Line 64, delete "10".

Signed and Sealed this

Sixteenth Day of August, 2005

JON W. DUDAS
*Director of the United States Patent and Trademark Office*